United States Patent [19]
Toma et al.

[11] Patent Number: 5,612,459
[45] Date of Patent: Mar. 18, 1997

[54] PRODUCTION AND CHARACTERISTICS OF ANTI-TEICOPLANIN POLYCLONAL ANTIBODY

[76] Inventors: Emil Toma, 150 Berlioz, #607, Iles des Soeurs, Québec, Canada, H3E 1K9; Madeleine Ravaoarinoro, 3511 Charles Daoust, #402, Chomedey, Québec, Canada, H7V 3Z5

[21] Appl. No.: 316,368

[22] Filed: Oct. 3, 1994

Related U.S. Application Data

[63] Continuation of Ser. No. 55,364, May 3, 1993, abandoned.

[51] Int. Cl.$^6$ .................................................. C07K 16/00
[52] U.S. Cl. ..................... 530/389.8; 436/547; 424/450; 424/184.1
[58] Field of Search ....................... 530/389.8; 424/450, 424/184.1; 436/547

[56] References Cited

FOREIGN PATENT DOCUMENTS

| | | |
|---|---|---|
| 2003325 | 5/1990 | Canada . |
| 1276880 | 11/1990 | Canada . |

OTHER PUBLICATIONS

Aguado et al., Immunobiol. vol. 184, pp. 113–125 (1992).

Bradford, M., "A Rapid and Sensitive Method for the Quantitation of Microgram Quantities of Protein Utilizing the Principle of Protein–Dye Binding", Analytical Biochemistry 72, pp. 248–54 (1976).

Szoka, F., Jr. et al, "Procedure for Preparation of Liposomes with Large Internal Aqueous Space and High Capture by Reverse–Phase Evaporation", Proc. Natl. Acad. Sci. USA., vol. 75, No. 9, pp. 4194–98, Sep. 1978.

Bangham, A.D., et al, "Preparation and Use of Liposomes as Models of Biological Membranes", Methods in Membrane Biology, vol. 11, 1974, pp. 1–68.

Ravaoarinoro M. et al., *91st ASM Abstract A–130*, 1991.

*Primary Examiner*—Toni R. Scheiner
*Attorney, Agent, or Firm*—Jacobson, Price, Holman & Stern, PLLC

[57] ABSTRACT

The present invention relates to antiteicoplanin polyclonal antibodies raised against a composition consisting of teicoplanin encapsulated in negatively-charged liposomes and the antibodies are not immunoreactive with any other antibiotics. The present invention relates to a method for determining the amount of teicoplanin in a biological sample, which comprises the steps of a) incubating anti-teicoplanin antiserum of the present invention with a biological sample containing an unknown amount of teicoplanin on a solid support; b) incubating anti-teicoplanin polyclonal antibodies of the present invention in serum with a standard containing a known amount of teicoplanin on a solid support; and c) determining the presence or absence of agglutination in step a) and b) whereby determining the unknown amount of teicoplanin present in the biological sample by comparing with the complete inhibition of agglutination of step b).

1 Claim, 3 Drawing Sheets

5,612,459

PRODUCTION AND CHARACTERISTICS OF ANTI-TEICOPLANIN POLYCLONAL ANTIBODY

This application is a continuation of application Ser. No. 08/055,364, filed May 3, 1993, now abandoned.

BACKGROUND OF THE INVENTION (a) Field of the Invention

The invention relates to the production and characteristics of anti-teicoplanin polyclonal antibodies and immunoassays for measuring teicoplanin.

(b) Description of Prior Art

Teicoplanin is the international non-proprietary name (INN) of the antibiotic substance formerly named teicomicin which is obtained by cultivating the strain *Actinoplanes teichomyceticus* (nov. sp. ATCC 31121) in a culture medium containing assimilable sources of carbon, nitrogen and inorganic salts. Canadian Patent Application 2,003,325 laid-open on May 22, 1990, in the name of Gruppo LePetit S.p.A., describes a process for preparing teicoplanin amides.

Teicoplanin, a novel glycopeptide antibiotic of the vancomycin class, is undergoing clinical investigation in some countries for the treatment of gram-positive infections.

Several methods of measuring serum teicoplanin or monitoring its therapeutic concentrations, have recently been developed, including microbiological assay, high pressure liquid chromatography, a solid phase enzyme receptor assay, a receptor-antibody sandwich assay and a fluorescence polarization immunoassay. Each method has some advantages and some limitations.

Methods known so far for determining antibiotic substances and in particular teicoplanin and the other antibiotics of the vancomycin class are mainly based on HPLC, and bioassays on susceptible microorganisms. In view of the current therapeutic use or advanced clinical study of some of these antibiotics, there is a need for assay methods for their determination in fluids, especially biological fluids, which would be specific, rapid, easy, reliable and suitable for automation.

In particular, the detection of these substances in body exudates, bronchial expectorates, pus, skin samples from burned patients, etc., is particularly difficult with known techniques since false-positive results are often obtained.

Canadian Patent 1,276,880 issued on Nov. 27, 1990, in the name of Gruppo LePetit S.p.A. describes a sandwich assay for determining a substance capable of binding to a D-Alanyl-D-Alanine dipeptide or a D-Alanyl-D-Alanine carboxy terminal oligopeptide. This sandwich assay can be used to determine a glycopeptidic antibiotic of the vancomycin class or a derivative or aglycon thereof. The assay combines the high selectivity of a suitable D-Alanyl-D-Alanine derivative for the antibiotics of the vancomycin class and the specificity of an antibody directed against the antibiotic of the class to be tested. The antibodies specifically directed to the substance to be determined are antibodies elicited in an animal by injection of a suitable conjugate of the substance to be tested. The antibody production was found unacceptable when following conventional antisera techniques. Several attempts were made to enhance the antibody production, such as combining the antigen to a protein such as bovine serum albumin (BSA). The antibody production has not reached a sufficient level to be commercially useful.

Antibodies to antibiotics are necessary for immunoassays to analyse cross-reactions and for other purposes. Several recent communications deal with the production of antibodies in rabbits and humans immunized with various antibiotics (penicillins, cephalosporins, aminoglycosides, clindamycine, amphotericin-B, etc.)

In these studies, antibiotics were conjugated with suitable proteins carriers such as bovine or human gamma-globulin and then emulsified in Freund's complete adjuvant. The quantity, titer and specificity of these antibodies appeared to be sufficient. However, antibody production in rabbits with antibiotics alone appeared to be insufficient. Some antibiotics showed the property of haptens. Others such as moxalactam, were much less immunogenic in rabbits.

It would be highly desirable to be provided with a method of producing anti-teicoplanin antibodies to a high level.

Liposomes are known as adjuvant in antigens preparations to enhance antibody response. Liposomes are concentric spheres consisting of phospholipid bilayers separated by aqueous compartments.

It would be highly desirable to be provided with a method of producing antibodies to antibiotics using liposomes.

It would be highly desirable to be provided with an antibody against teicoplanin which could be used in an immunoassay for measuring the amount of teicoplanin present in a sample.

SUMMARY OF THE INVENTION

One aim of the present invention is to provide for a method of producing polyclonal antibodies to antibiotics using antibiotic-containing-liposomes.

Another aim of the present invention is to provide for a anti-teicoplanin polyclonal antibody.

Another aim of the present invention is to provide for an immunoassays for measuring teicoplanin in a sample.

In accordance with the present invention there is provided a method for producing polyclonal antibodies specific to teicoplanin, which comprises the steps of: a) immunizing an animal with an immunogen liposomal composition encapsulating teicoplanin in an amount sufficient to elicit an immunogenic reaction from said animal; b) allowing incubation for a time sufficient for said immunogenic reaction to occur; c) collecting sera from said immunized animal; and d) isolating the polyclonal antibodies from said sera by centrifugation.

In accordance with the present invention there is provided anti-teicoplanin polyclonal antibodies raised against a composition comprising teicoplanin encapsulated in negatively-charged liposomes, said antibodies are not immunoreactive with any other antibiotics.

More specifically, and in accordance with the present invention there is provided anti-teicoplanin polyclonal antibodies raised against a composition comprising teicoplanin solubilized in negatively charged liposomes of egg lecithin, dicetyl phosphate and cholesterol in a molar ratio of 7:2:1, said antibodies are not immunoreactive with any other antibiotics.

In accordance with the present invention there is provided a method for determining the amount of teicoplanin in a biological sample, which comprises the steps of a) incubating anti-teicoplanin antiserum of the present invention with a biological sample containing an unknown amount of teicoplanin on a solid support for a time sufficient to allow for an immunogenic reaction to occur; b) incubating anti-teicoplanin polyclonal antibodies of the present invention in serum with a standard containing a known amount of teicoplanin on a solid support for a time sufficient to allow for an immunogenic reaction to occur; and c) determining the presence or absence of agglutination in step a) and b) whereby determining said unknown amount of teicoplanin present in said biological sample by comparing with the complete inhibition of agglutination of step b).

In particular, in accordance with the present invention there is provided a method for determining the amount of teicoplanin in a biological sample, which comprises the steps of: a) incubating at least the polyclonal antibodies of the present invention or fragments thereof, latex particles or other agglutination components, and an unknown amount of teicoplanin present in a biological sample; b) incubating at least the polyclonal antibodies of claim 2 or fragments thereof, latex particles or other agglutination components, and a known amount of teicoplanin; c) determining the presence or absence of agglutination in step a) and b) whereby determining said unknown amount of teicoplanin present in said biological sample by comparing with the complete inhibition of agglutination of step b).

In accordance with the present invention there is provided a kit for determining the amount of teicoplanin in a biological sample by comparing the presence or absence of agglutination of anti-teicoplanin antibodies incubated with said biological sample with a standard curve obtained with a known amount of teicoplanin, said kit is adapted to be used according to the method of the present invention and comprises: I) polyclonal antibodies of the present invention or fragments thereof; II) latex particles or agglutination components; and III) a known amount of teicoplanin, whereby said standard curve is obtained.

Accordingly, the most preferred solid support is a latex slide, such as the test card with 6 wells STREPSLIDE™ (sold by NCS Diagnostics Inc., Ontario, Canada).

DETAILED DESCRIPTION OF THE INVENTION

Figure 1A:
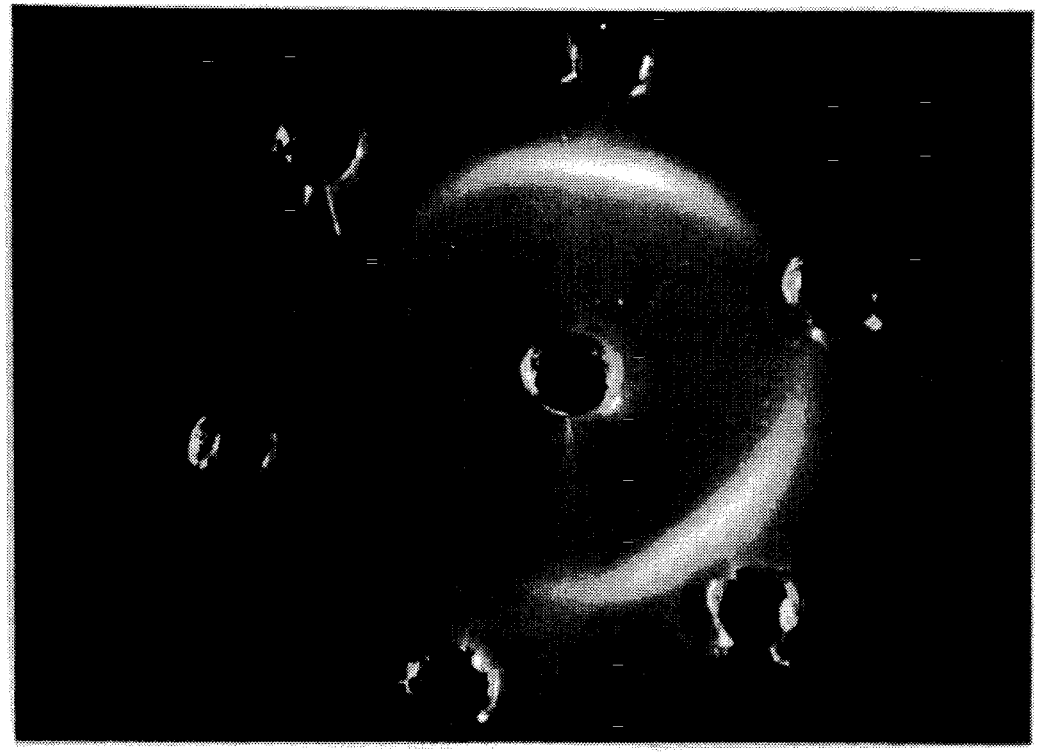
FIGS. 1A to 1D show reactivity of diluted antiteicoplanin polyclonal antibodies of the present invention in serum against teicoplanin solution by immunodiffusion test.

Teicoplanin belongs to a class of antibiotics referred to as the "vancomycin class" which encompasses the following antibiotics (in addition to teicoplanin): Actaplanin, ristocetin, avoparcin, actinoidin, antibiotic LL-AM-374, antibiotic A477, antibiotic OA 7653, antibiotic A 35512 B, amongst others, as well as the individual factors, derivatives and aglycons thereof.

The use of liposomes as adjuvants was considered in order to produce antibodies to teicoplanin. In accordance with the present invention, the following procedure was used to arrive at the anti-teicoplanin antibodies:

1) to assess the adjuvant effect of liposomes in relation to Freund's complete adjuvant (FCA);

2) to compare the efficacy of two types of antibiotic-containing positively- and negatively-charged liposomes;

3) to determine cross-reactivity between antibodies and other antibiotics.

I. PRODUCTION OF POLYCLONAL ANTIBODIES TO ANTIBIOTICS

Chemicals

Teicoplanin sold by Merrell Dow Research Institute, Merrell Dow Pharmaceuticals Inc., Cincinnati, Ohio;

Gentamicin sold by Schering Corp., Kenilworth, N.J.;

Tobramycin and vancomycin sold by Eli Lilly Research Laboratories, Indianapolis, Ind.;

Ceftazidime sold by Glaxo Laboratories, Greenford, Middlesex, England; and

Positive liposome kit (egg lecithin, stearylamine, cholesterol) and negative liposome kit (egg lecithin, dicetyl phosphate, cholesterol) sold by Avanti Polar Lipids, Birmingham, Ala.

Preferably the negatively-charged liposomes are used with the egg lecithin, dicetyl phosphate, cholesterol in a molar ratio of 7:2:1.

A convenient host animal for producing a conventional antiserum, which can then be purified or fractionated to isolate the IgGs, is the rabbit. However, other non-human mammalian animals can be used in accordance with the present invention, such as rat.

Experimental Procedure

Emulsions of teicoplanin (T) in Freund's Complete adjuvant (FCA) or Freund's Incomplete adjuvant (FIA) are prepared to give a final antibiotic concentration of 10 mg/ml. Teicoplanin is encapsulated in liposomes (L) as described below (Ravaoarinoro M. et al., 91st ASM Abstract A-130, 1991).

The production of antibiotic-containing liposomes used as drug-carriers is affected by the low drug entrapment rate and stability. In order to improve amikacin and teicoplanin liposomal entrapment and stability, the following has been assessed:

a) the efficacy of 2 liposomal preparation methods (A=Bangham's method; B=reverse phase-evaporation method); and the effect of structure (i.e. unilamellar resides-ULV or multilamellar vesicles-MLV), electrical charge and addition of cryoprotectant.

Amikacin content of liposomes is determined by EMIT assay and teicoplanin by microbiological assay after diluting the liposome suspension in the presence of 1% TRITON X-100™ ULV are prepared by sonication. Negatively stained liposomes are examined at an electron microscope.

Higher encapsulation rate is obtained with the Bangham's method and negative MLV for both amikacin (45% vs 15%) and teicoplanin (34% vs 26%). Amikacin liposomal entrapment rate was higher than that of teicoplanin whatever method used, structure or phospholipid composition. Addition of 250 mM sucrose to amikacin or teicoplanin encapsulated liposomes prepared by the Bangham's method prevents a decrease of antibiotic content in only negative ULV and MLV after 3 month storage at −70° C. These results may be useful in guiding effective antibiotic encapsulation preparation and storage.

Female white New Zealand rabbits (Groups A to D) weighing 1 to 2 kg are immunized with an immunogen and according to the schedule of Table 1.

All groups of rabbits are bled 2 weeks after of the last immunization.

TABLE 1

Rabbit Immunization Schedule

| Immunization Day | Administration Mode | Route | Volume |
|---|---|---|---|
| Group A | | | |
| D0 | T + FCA | ID | 1.0 ml |
| D14 | T + FIA | SC | 0.5 ml |
| D21 | T + FIA | SC | 0.5 ml |
| D40 | T + FIA | SC | 0.5 ml |
| D60 | T + FIA | SC | 0.5 ml |
| Group B | | | |
| D0 | T + L | IV | 3 × 0.3 ml |
| D21 | T + L | IV | 0.5 ml |
| Group C | | | |
| D0 | T | IV | 0.3 ml |
| D2 | T | IV | 0.3 ml |
| D4 | T | IV | 0.3 ml |
| D14 | T | IV | 0.5 ml |
| D40 | T | IV | 0.5 ml |
| D60 | T | IV | 0.5 ml |
| Group D | | | |
| D0 | L | IV | 0.3 ml |
| D2 | L | IV | 0.3 ml |
| D4 | L | IV | 0.3 ml |
| D14 | L | IV | 0.5 ml |
| D40 | L | IV | 0.5 ml |
| D60 | L | IV | 0.5 ml |

ID: intradermal; SC: subcutaneous; IV: intravenous.

The antibody produced from two types of antibiotic-containing liposomes, positively- and negatively-charged, are compared.

Rabbits (in groups of 4) are injected intravenously on day 1 and 21 with 1 ml (10 mg/ml) of teicoplanin encapsulated respectively in negatively and positively-charged liposomes and assayed according to the schedule of Table 2. The animals are bled at timed intervals, and teicoplanin antibodies were assayed in sera by the hemagglutination (HA) and by the immunodiffusion (ID) tests or the Ouchterlony's method. The Ouchterlony's Petri dish method is performed to determine the specificity of rabbit anti-teicoplanin serum and cross-reactivity with other antibiotics.

Protein in partially purified serum is estimated by Bradford's method using the BIO-RAD™ protein assay kit (Bio-Rad Laboratories, Richmond, Calif.) with bovine serum albumin as standard.

The amounts and forms of teicoplanin used to immunize the rabbits in accordance with one embodiment of the present invention, with their results illustrated in the FIGS. 1A to 1D and 2, are as follows:

FIG. 1A:
well no. 7: 10 μl of teicoplanin (20 mg/ml).
well no. 1: 10 μl of serum from rabbit immunized with teicoplanin encapsulated in negatively-charged liposomes (dilution 1:4).
well no. 3: 10 μl of serum from rabbit immunized with teicoplanin encapsulated in negatively-charged liposomes (dilution 1:8).
well no. 6: 10 μl of serum from rabbit immunized with teicoplanin encapsulated in negatively-charged liposomes (dilution 1:16).

Figure 1B:
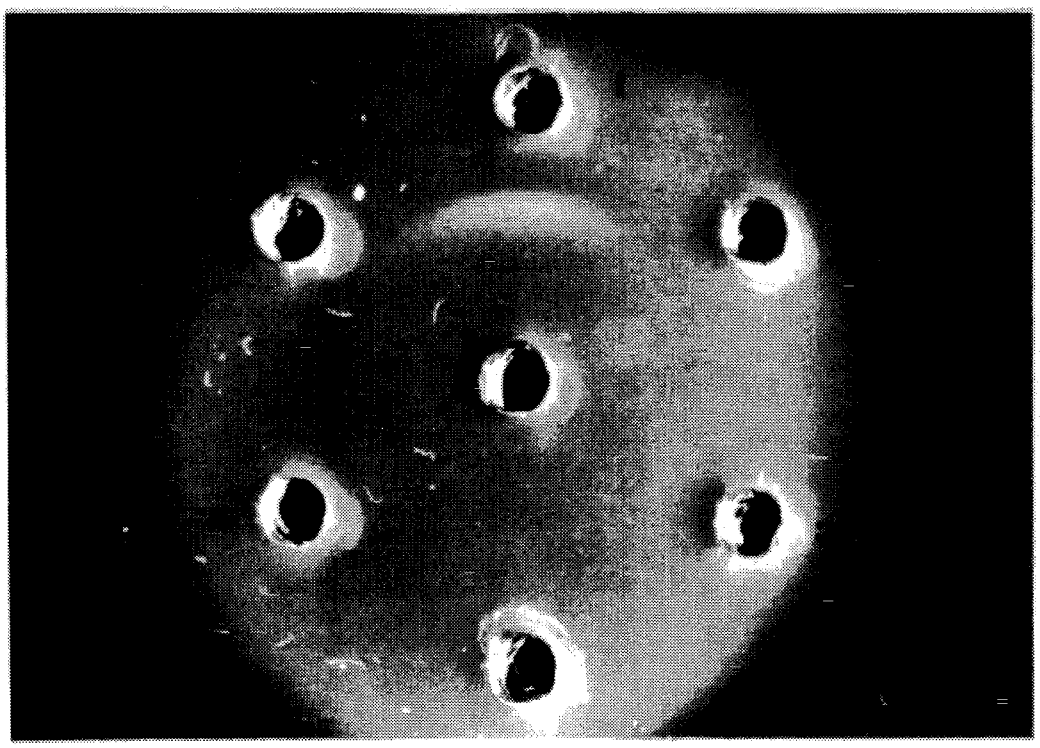

FIG. 1B:
well no. 7: 10 μl of teicoplanin (20 mg/ml).
well no. 1: 10 μl of serum from rabbit immunized with teicoplanin encapsulated in positively-charged liposomes (dilution 1:4).
well no. 3: 10 μl of serum from rabbit immunized with teicoplanin encapsulated in positively-charged liposomes (dilution 1:8).
well no. 6: 10 μl of serum from rabbit immunized with teicoplanin encapsulated in positively-charged liposomes (dilution 1:16).

Figure 1C:
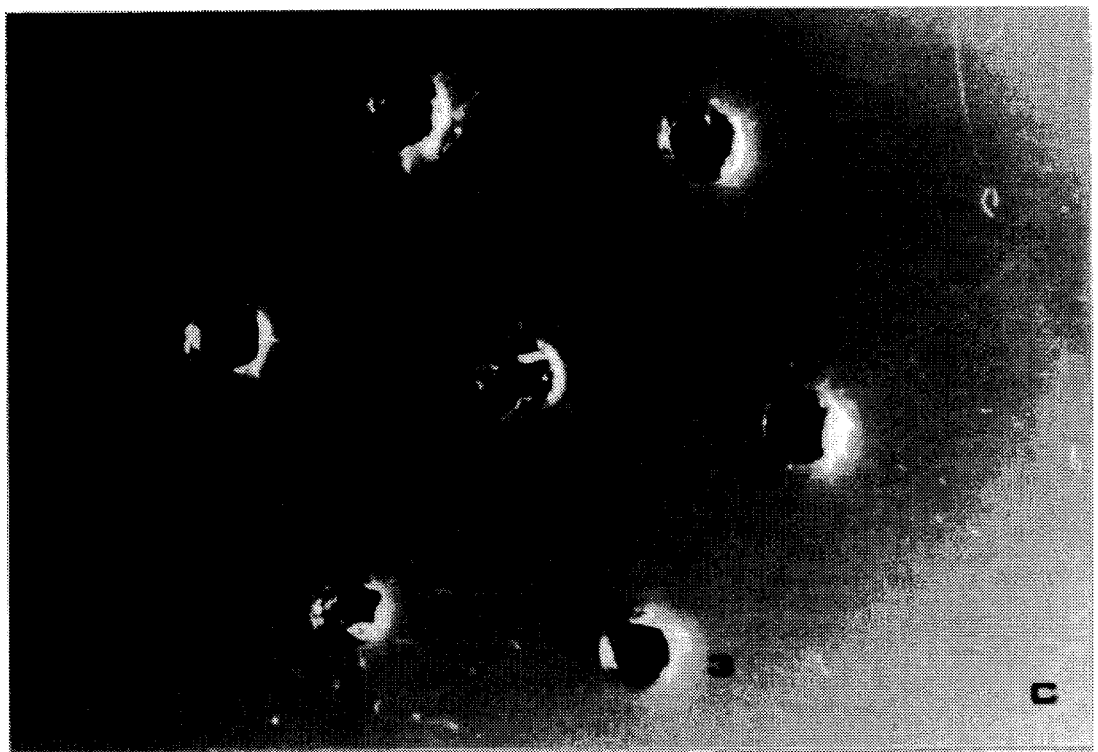

FIG. 1C:
well no. 7: 10 μl of teicoplanin (20 mg/ml).
wells no. 1 & 3: 10 μl of serum from rabbit immunized with negatively-charged liposomes alone (dilution 1:4).
wells no. 4 & 5: 10 μl of serum from rabbit immunized with positively-charged liposomes alone (dilution 1:4).

Figure 1D:
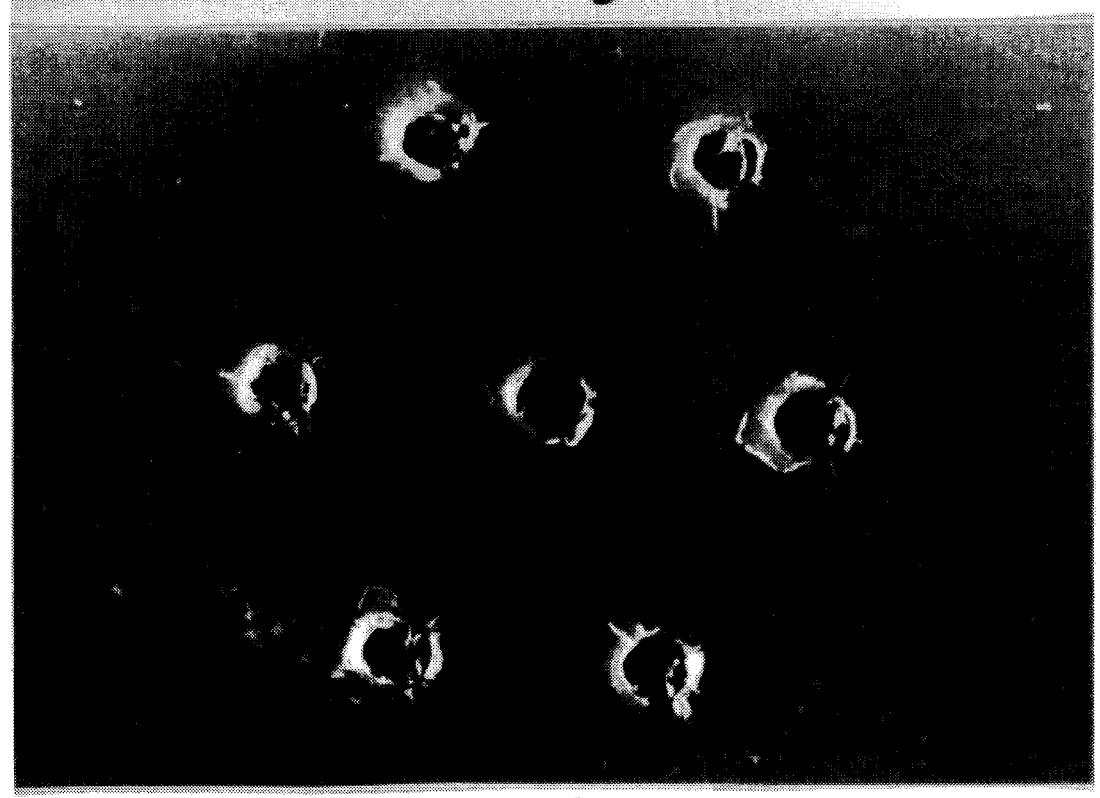

FIG. 1D:
well no. 7: 10 μl of straphylococcal ribitol teichoic acid (purified extract)
well no. 1, 2, 3, 4, 5, and 6: 10 μl of anti-staphylococcal ribitol teichoic acid.

Figure 2:
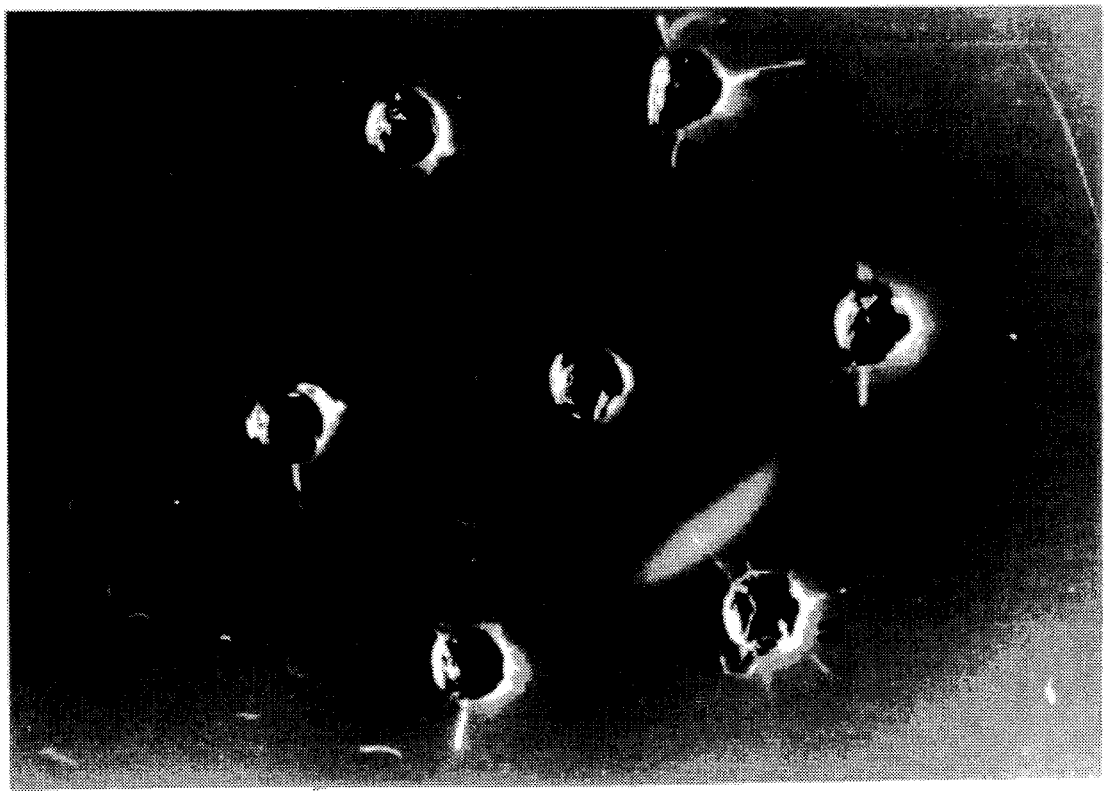
FIG. 2 shows the specificity of antisera raised in rabbits against teicoplanin encapsulated in negatively charged liposomes by immunodiffusion test.

FIG. 2:
well no. 7: 10 μl of anti-teicoplanin sera.
well no. 1: 10 μl of gentamicin (20 mg/ml).
well no. 2: 10 μl of tobramicin (20 mg/ml).
well no. 3: 10 μl of teicoplanin (20 mg/ml).
well no. 4: 10 μl of amikacin (20 mg/ml).
well no. 5: 10 μl of ceftazidime (20 mg/ml).
well no. 6: 10 μl of vancomycin (20 mg/ml).

TABLE 2

Antibody to Teicoplanin Encapsulated Respectively in Positively- And Negatively-Charged Liposomes

| Days after injection | Teicoplanin-negative liposomes | | | Teicoplanin-positive liposomes | | |
|---|---|---|---|---|---|---|
| | HA titer[a] | ID[b] | IgG[c] | HA titer[a] | ID[b] | IgG[c] |
| 14 | 4 | + | ND | 2 | + | ND |
| 22 | 16 | + | 14.5 | 2 | + | 3.520 |
| 75 | 2 | − | ND | 0 | 0 | ND |

[a]Titers represent the reciprocity of dilution with complete hemagglutination.
[b]Presence or absence of precipitate bands expressed + or −.
[c]Protein concentration (mg/ml) of partially purified serum determined by Bradford's method.
ND: not done.

Rabbits (in groups of 4) are injected subcutaneously with immunogen A, or intravenously with immunogen B, C and D. Immunogens A, C and D are administered on days 0, 14, 40, and 60 as shown in Table 3. Immunogen B is given on days 0, and 21.

Animals are bled at timed intervals and teicoplanin antibodies are assayed in sera by the hemagglutination (HA) and immunodiffusion tests (ID).

TABLE 3

Comparison of Teicoplanin-Encapsulated Liposome with Other Adjuvant Formulations

| Adjuvant formulation | Days after 1st injection | | | | | | | | | |
|---|---|---|---|---|---|---|---|---|---|---|
| | 14 | | 21 | | 40 | | 60 | | 75 | |
| | HA[a] | ID[b] | HA | ID | HA | ID | HA | ID | HA | ID |
| A- T + FCA | 4 | + | ND | ND | 2 | − | 2 | − | 2 | − |
| B- T + L | ND | ND | 16 | + | ND | ND | ND | ND | 4 | + |
| C- T | 4 | + | ND | ND | 0 | − | 0 | − | 0 | − |
| D- L | 0 | − | 0 | − | 0 | − | 0 | − | 0 | − |

[a]titers represent the reciprocity of dilution with complete hemagglutination.
[b]Presence or absence of precipitate bands expressed as + or −.
ND: not done; T: teicoplanin; FCA: Freud's complete adjuvant; L: liposome Antibodies to teicoplanin were easily obtained. The highest teicoplanin antibody titer was achieved with negatively-charged liposomes injected intravenously and with only 2 immunizations. In contrast, the titers were lower with positively-charged liposomes containing teicoplanin, teicoplanin suspended in FCA or teicoplanin alone and more than 5 intravenously injections were necessary.

No cross-reaction was noted between teicoplanin antibodies and other antibiotics.

II. ASSAY TO MEASURE TEICOPLANIN

The present invention also relates to a latex agglutination inhibition method to measure teicoplanin in biological fluids using an anti-teicoplanin antibody of the present invention.

In accordance with the present invention, this assay is based on slide latex agglutination inhibition: teicoplanin-sensitized latex particles react to anti-teicoplanin antibodies. The addition of serum containing teicoplanin inhibits the agglutination reaction. Teicoplanin is measured by comparing inhibition of different known concentrations by anti-teicoplanin antibodies.

Material & Method
  1- Bioassay method
  Mueller Hinton Agar (BBL Microbiology Systems, Cockeysville, Md.);
  Plates: 100 mm in diameter; (DIFCO
  Bacillus subtilis spore suspensions Laboratories, Detroit, Mich.);
  Incubation: 35° C. for 16–18 H; Standard curve solutions:
  Stock solution: 960 ug/ml in 0.1 m sodium
  phosphate buffer of pH 7.4; and
  Various concentrations (96, 48, 24, 12, 6.0 and 3.0 ug/ml) in pooled human sera.
  2- Slide latex agglutination-inhibition
  This assay is based on slide latex agglutination inhibition: teicoplanin-sensitized latex particles react to the anti-teicoplanin antibodies of the present invention. The addition of serum containing teicoplanin inhibits the agglutination reaction. Teicoplanin concentration is measured by comparing inhibition of different known concentrations by anti-teicoplanin antibodies.

Anti-teicoplanin antiserum was added on a slide (test card with 6 wells called STREPSLIDE™, sold by NCS Diagnostics Inc., Ontario, Canada), enabling the teicoplanin present in the serum dilution and the standards to react with antibody. Teicoplanin-coated latex particles were then added to the well. After mechanical mixing, the slide was held under a high intensity lamp and the presence or absence of agglutination was determined for the standard and the sera sample.

Latex polystyrene particles (Seradyn Inc., Indianapolis, Ind.) having a size ranging from 0.295, 0.495 and 0.825 um are used at a concentration of 0.25, 0.50 and 1.0% (w/v).

The passive coating of the latex particles is effected with 2,5 and 10 mg/ml of teicoplanin, respectively with 50 mm phosphate buffer of pH 7.4.

Test card with 6 wells called STREPSLIDE™ (sold by NCS Diagnostics Inc., Ontario, Canada) were used.

The latex agglutination inhibition procedure in accordance with the present invention is conducted according to the following steps:
a) adding 50 ul diluting serum to 50 ul anti-teicoplanin serum;
b) incubating for 20 min at room temperature with constant shaking;
c) adding 50 ul teicoplanin-latex particle reagent; and
d) incubating for 10–15 min at room temperature with constant shaking.

Serum samples

Quantitation in ten replicates of each sample (6.1) was undertaken in a blinded fashion by bioassay and slide latex agglutination inhibition, respectively.

Assay reading

The amount of teicoplanin in an unknown sample may be quantitated by reference to a standard concentration (3, 6, 12, 25, 50, 100 µg/ml). Controls are also run to ensure that the antiserum and teicoplanin latex particles are agglutinating properly in the absence of teicoplanin.

Statistical analysis

Linear regression analysis is used to determine the correlation coefficient of the slide latex agglutination-inhibition assay and bioassay.

The latex agglutination reaction to anti-teicoplanin rabbit serum is determined using different sizes of latex particles coated with 2 mg/ml of teicoplanin, the results of which are shown in Table 4. The assay is effected in four replicates and the presence or absence of agglutination is expressed as + or −.

TABLE 4

Latex Agglutination Reaction Coated with 2 mg/ml of Teicoplanin

| Latex Concentrations | Latex particles size (um) | | |
|---|---|---|---|
| % (w/v) | 0.295 | 0.489 | 0.825 |
| 0.25 | +/− | +/− | +/− |
| 0.50 | ++ | − | − |
| 1.0 | +/− | − | − |

Latex agglutination reactions is effected with anti-teicoplanin rabbit serum using 0.5% (w/v) latex particles suspension of three different sizes and coated with different teicoplanin concentrations, the results of which are listed in Table 5. The assay is effected in four replicates and the presence or absence of agglutination is expressed as + or −.

TABLE 5

Latex Agglutination Reaction
Coated with Different Teicoplanin Concentrations

| Teicoplanin concentrations (mg/ml) | Latex particles size (um) | | |
|---|---|---|---|
| | 0.295 | 0.489 | 0.825 |
| 2.0 | + | +/− | +/− |
| 5.0 | +++ | + | +/− |
| 10.0 | + | +/− | +/− |

Six different teicoplanin concentrations are assayed in ten replicates to compare the latex agglutination-inhibition assay (LAI) and the bioassay. The correlation coefficient is 0.90.

TABLE 6

Comparative Study

| Teicoplanin concentrations (μg/ml) | LAI % of inhibition | Bioassay (zone diameter, mm) |
|---|---|---|
| 100 | 100 | 90.4 |
| 50 | 80 | 48.6 |
| 25 | 50 | 26.9 |
| 12 | 10 | 9.5 |
| 6 | 1 | 4.8 |
| 3 | 1 | 2.7 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for producing polyclonal antibodies specific to teicoplanin, which comprises the steps of:

a) immunizing an animal with an immunogen liposomal composition consisting of teicoplanin encapsulated in negatively- or positively-charged liposomes, wherein said composition is in a concentration of about 10 to 20 mg/ml to elicit an immunogenic reaction from said animal;

b) allowing incubation for a time sufficient for said immunogenic reaction to occur;

c) collecting sera from said immunized animal; and d) isolating the anti-teicoplanin polyclonal antibodies from said sera by centrifugation.

* * * * *